(12) United States Patent
Keller et al.

(10) Patent No.: US 7,001,432 B2
(45) Date of Patent: Feb. 21, 2006

(54) INTERVERTEBRAL PROSTHESIS

(75) Inventors: Arnold Keller, Kayhude (DE); Paul C. McAfee, Baltimore, MD (US)

(73) Assignee: Cervitech, Inc., Rockaway, NJ (US)

( * ) Notice: Subject to any disclaimer, the term of this patent is extended or adjusted under 35 U.S.C. 154(b) by 171 days.

(21) Appl. No.: 10/340,726

(22) Filed: Jan. 13, 2003

(65) Prior Publication Data

US 2003/0176923 A1 Sep. 18, 2003

(30) Foreign Application Priority Data

Mar. 12, 2002 (EP) .................. 02005631
Mar. 12, 2002 (EP) .................. 02005632

(51) Int. Cl.
*A61F 2/44* (2006.01)

(52) U.S. Cl. .................. 623/17.14; 623/17.15

(58) Field of Classification Search ............. 623/17.11, 623/17.14, 17.15, 17.16, 20.15, 19.12, 20.22, 623/20.23, 20.27, 20.28, 21.13, 21.16, 23.4; 606/61
See application file for complete search history.

(56) References Cited

U.S. PATENT DOCUMENTS

| | | | |
|---|---|---|---|
| 5,425,773 A | 6/1995 | Boyd et al. | |
| 5,888,223 A * | 3/1999 | Bray, Jr. | .................. 623/17.16 |
| 6,302,914 B1 * | 10/2001 | Michelson | ............... 623/17.16 |

FOREIGN PATENT DOCUMENTS

| | | |
|---|---|---|
| EP | 0 471 821 B1 | 6/1994 |
| EP | 0 747 025 A1 | 12/1996 |
| FR | 2 718 635 | 10/1995 |
| WO | 99/65412 A1 | 12/1999 |
| WO | 00/53127 A1 | 9/2000 |
| WO | 01/01893 A1 | 1/2001 |
| WO | 01/64142 A1 | 9/2001 |

* cited by examiner

*Primary Examiner*—Brian E Pellegrino
(74) *Attorney, Agent, or Firm*—Morrison & Foerster LLP

(57) ABSTRACT

An intervertebral prosthesis, in particular for the cervical spine, includes a first cover plate to be connected to a first vertebral body, a second cover plate to be connected to the second vertebral body, and a prosthesis core which forms an articulation with the second cover plate. The prosthesis core is held by a seat of the first cover plate which is designed as a guide device. The core can be pushed into the guide device from the ventral side in the anterior-posterior (AP) direction relative to the first cover plate. A limit-stop plate is provided on the ventral edge of the first cover plate. This limit-stop plate is displaceable in a slide guide between a locking position and a nonlocking position.

19 Claims, 5 Drawing Sheets

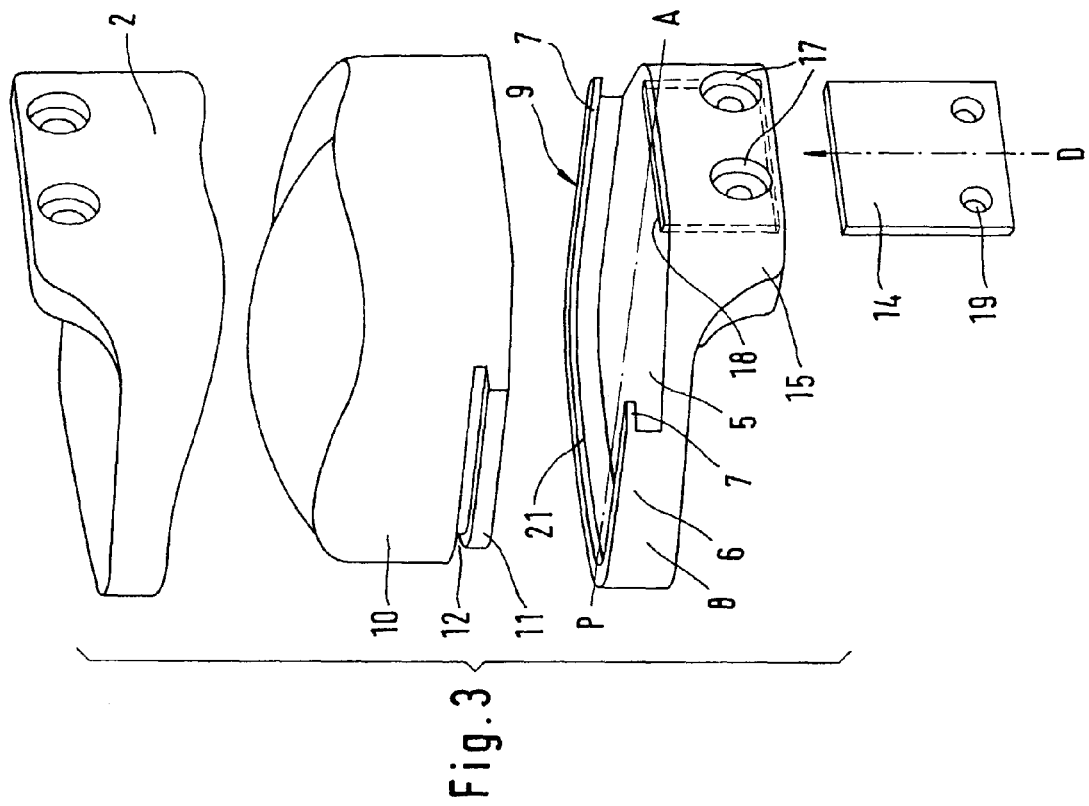
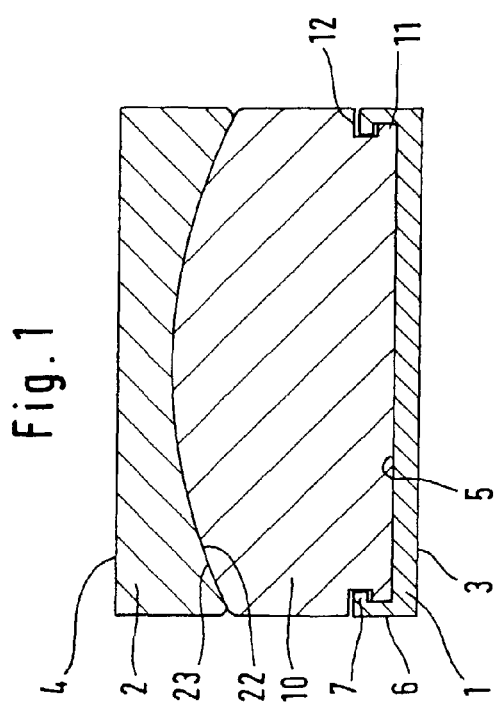
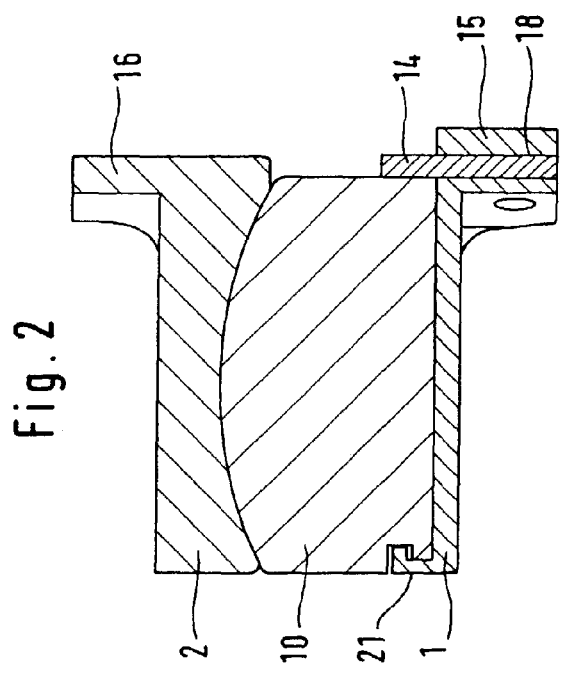

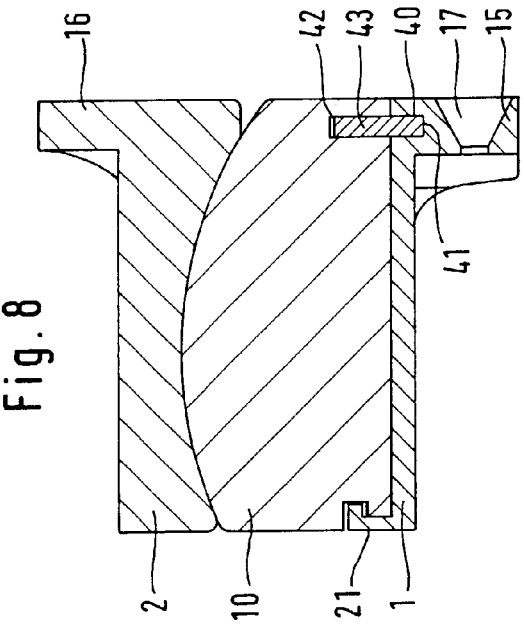
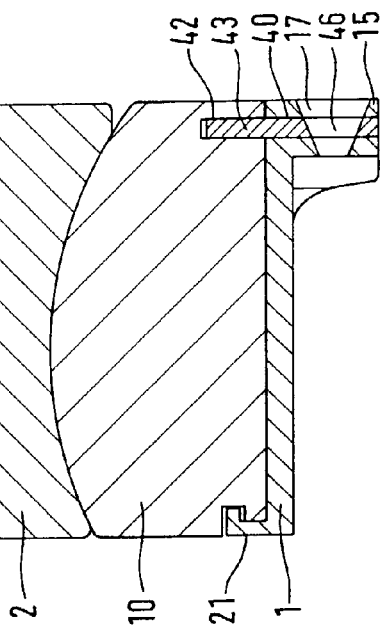
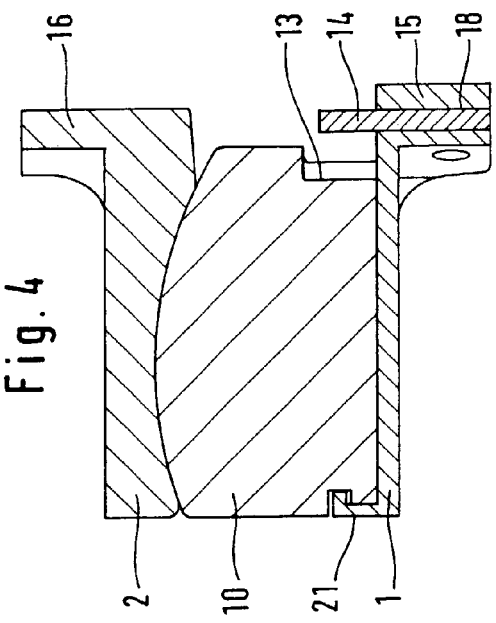
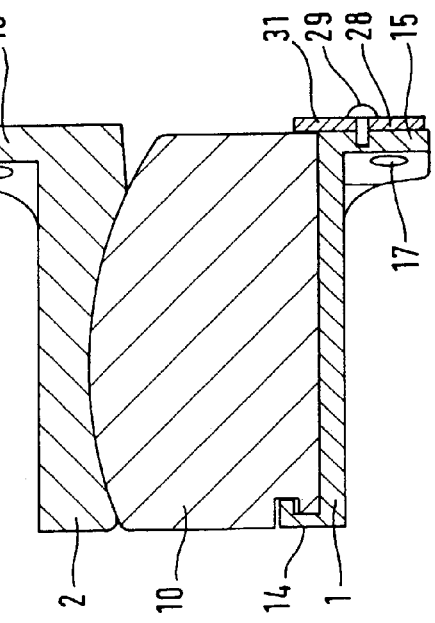

INTERVERTEBRAL PROSTHESIS

FIELD AND BACKGROUND OF THE INVENTION

Intervertebral prostheses are used for replacing intervertebral disks. They comprise two cover plates whose outer surfaces are designed for connection to adjacent vertebral bodies, and of an articulation device enclosed by the cover plates. In a known prosthesis type (WO 01/01893, FR-A-2718635), the upper cover plate forms a concavely spherical articulation surface on its inner side, which cooperates with the convexly spherical top surface of a prosthesis core of polyethylene in order to form an articulation. The flat underside and the edge of the core are received with matching fit in a seat which is formed by the lower cover plate. This seat comprises a plane bottom surface and a vertical edge which surrounds the latter on three sides (laterally and dorsally). On the sides, the edge is formed by two undercut edge ridges which extend substantially in the anterior-posterior (hereinafter "AP") direction and to which complementary projecting ridges or grooves on the edge of the prosthesis core correspond. On the ventral side, the edge of the cover plate is open so that the prosthesis core can be pushed like a drawer into the edge of the cover plate, in a movement extending in the AP direction. In the pushed-in state, the prosthesis core is secured against lifting by means of the interaction of the projecting ridges and grooves of the cover plate and of the prosthesis core. In particular, it cannot move dorsally from the intended position toward the spinal cord when the cover plates spread open dorsally during a flexion movement.

There are known intervertebral prostheses in which the edge of the lower cover plate is also closed ventrally (EP-B-471821, U.S. Pat. No. 5,425,773). However, this has the disadvantage that the prosthesis core either cannot be inserted between the cover plates after they have been implanted or is not secured against lifting in the seat of the lower cover plate. By contrast, the invention relates to the type of prosthesis in which the seat of the lower cover plate is designed as a ventrally open push-in guide for the prosthesis core, so that this can be inserted into the prosthesis after the cover plates have been implanted.

To ensure that the prosthesis core cannot escape ventrally from the seat, a locking limit stop is provided in the known prostheses of this type (FR-A-2 718 635, WO 01/01893). This locking limit stop consists of interacting projections and recesses in the underside of the prosthesis core, on the one hand, and in the bottom surface of the seat, on the other hand. To ensure that these can come into engagement with one another when the prosthesis core is pushed into the seat, the seat which is made of resilient plastic material must deform elastically before these elements lock together. The disadvantage of this is that the interlocking is in principle unsafe, because it can be released again by a corresponding elastic deformation of the prosthesis core. It is of course possible to improve the locking safety by giving the prosthesis core the greatest possible resistance to deformation. However, this makes it difficult for the operating surgeon to insert the prosthesis core into the seat. It can also happen that, for random reasons of which the operating surgeon remains unaware, the lock elements do not attain the lokking position, or do so incompletely, for example because a foreign body has been left in the locking recess or because a chance obstacle has meant that the prosthesis core has not been pushed far enough into the seat.

SUMMARY OF THE INVENTION

The object of the invention is therefore to make available an intervertebral prosthesis of the type described, in which the prosthesis core is held securely in the prosthesis and does not complicate the operation.

In order to allow the prosthesis core the AP movement which is necessary for pushing it into the seat, the seat is designed as a guide device with a direction extending in the AP direction. This guide device can be formed by parallel, lateral guide rails which lie opposite one another and between which the core is held in such a way that it can move only in the AP direction. The guide rails are in this case expediently undercut in order to interact with a ridge of the core engaging in the undercut. In this way, the core is prevented from lifting from the cover plate which is holding it. This has the advantage that the devices provided for limiting the movement of the core do not have to be very high, and there is therefore also no danger that they could impede the relative movement of the cover plates in relation to one another. To ensure that the core does not slide out of the guide area of the rails in the dorsal or ventral direction, suitable limit stops are provided. The limit stop for dorsal movement is expediently connected rigidly to the cover plate which forms the seat (i.e. the guide rails). On the ventral side, a limit stop against movement is provided which can be moved away from its locking position so that the core can be more easily fitted after implantation of the cover plate. The limit stop is subsequently fixed in the position in which it prevents the escape of the core.

On the ventral edge of the cover plate forming the seat, a slide guide is provided in or on which the limit stop is displaceable between a locking position and a nonlocking position. This satisfies the condition that the operating surgeon must move the limit stop deliberately into the locking position. The locking position of the limit stop is therefore reached with certainty.

In a particularly expedient embodiment, the slide guide is formed by a guide slot which extends transverse to the guide device and which receives the limit stop designed as a limit-stop plate.

For example, the guide slot can have a guide direction extending transverse to the plane of extension of the cover plate. That is to say, part of the limit-stop plate, in its locking position, engages in the slot and is held by the latter, and another part extends above the bottom surface of the seat in order to hold the prosthesis core securely in the seat. In the nonlocking position, it is lowered below the bottom surface of the seat into the slot or is completely removed from the latter via the top or bottom.

Instead of this, the guide slot can also have a guide direction extending parallel to the plane of extension of the first cover plate and transverse to the AP direction. In this case, the limit-stop plate is pushed into the guide slot from the side in order to reach the locking position.

In each case, safety devices should be present in order to secure the limit-stop plate in the locking position. Particularly reliable securing is afforded if the limit-stop plate has a fastening screw passing through it, so that the limit-stop plate can be removed from the securing position only if the screw has first been removed. For this purpose, the guide slot has at least one screw hole passing through it, and the limit-stop plate has a screw hole which is flush with the first-mentioned screw hole when the limit-stop plate is in its locking position. This embodiment is particularly advantageous if the guide slot lies in a securing flange which is provided on the ventral edge of the cover plate forming the seat.

Further securing, by which the limit-stop plate is secured against escape from the guide slot, is achieved when the prosthesis core has a part which covers the limit-stop plate held in the guide slot. This cover can be designed as a slot in the prosthesis core, which slot is flush with the guide slot when the prosthesis core has reached the intended position in the seat. The guide slot in the cover plate, on the one hand, and the flush slot in the prosthesis core, on the other hand, then form a recess for the limit-stop plate into which it can be easily pushed from the side.

In a further possibility of securing, the limit-stop plate has an easily bendable fastening lug which projects past the guide slot in the locking position in the direction of the guide slot. After insertion, this fastening lug is bent by the operating surgeon in such a way that it protrudes from the plane of the limit-stop plate and thereby makes the return movement in the guide slot impossible.

In another embodiment of the limit-stop plate according to the invention, it is not moved from the nonlocking position to the locking position in translation, but instead by a pivoting movement. In this case, the slide guide which receives the limit-stop plate is formed by a slide-guide surface extending transverse to the AP direction on the ventral edge of the cover plate, and by a pivot pin which issues from the slide-guide surface and on which the limit-stop plate is pivotably mounted. The limit-stop plate has a tongue which, in a locking pivot position of the limit-stop plate, protrudes above the bottom surface of the seat and thus prevents escape of the prosthesis core from the seat. In the nonlocking position, this limit-stop tongue is lowered below the bottom surface of the seat. The slide-guide surface on which the limit-stop plate is held is expediently formed by the front face of a securing flange. The latter also has at least one screw hole in the proximity of the pivot pin. According to the invention, the limit-stop plate can be used to secure the screw located in this screw hole, by engaging with a wing over the screw head located in the screw hole.

The limit stop according to the invention is suitable not only for those cases in which the prosthesis core assumes a fixed, immovable position in the seat, but also for those cases in which it is afforded freedom of movement, in particular in the AP direction. The guide device, formed by the seat, for the prosthesis core is then used not only for the insertion movement of the prosthesis core, but also for continuous mobility. This can be advantageous in particular in cervical spine prostheses, in which the articulation surface of the prosthesis core extends over substantially the whole cover plate. In these cases, it would in fact be desirable to keep the radius of curvature of the articulation surface to a minimum in order to keep the overall height of the prosthesis to a minimum. In such cases, an AP mobility of the prosthesis core can improve the approximation of the flexion properties of the prosthesis to the natural conditions. In a particular aspect of the inventive concept therefore, a system of intervertebral prostheses includes, in addition to those which have this AP mobility, other prostheses, preferably of corresponding external configuration, which do not have AP mobility between the prosthesis core and the cover plate holding it. This allows the physician to decide, during the operation, whether or not he wishes to provide AP mobility. The cover plates of the prostheses movable or immovable in the AP direction are expediently of uniform configuration, and only the core is different. However, provision can also be made for the prosthesis core, and the cover plate forming the articulation with it, to be uniform in all types, while the AP mobility is afforded by differences in the cover plate holding the prosthesis core. Finally, there is also the possibility that all three components are uniform, and that only the limit stop limiting the ventral movement of the prosthesis core in the AP direction is differently located.

Where the terms lower and upper cover plate are used here, this is not intended to imply that the cover plate forming the seat for the core would always have to be arranged at the bottom. Rather, the arrangement can also be chosen the other way round. The claims therefore talk more generally of a first cover plate and a second cover plate.

BRIEF DESCRIPTION OF THE DRAWINGS

Preferred embodiments are explained below with reference to the drawings, in which:
FIG. 1 shows a frontal cross section,
FIG. 2 shows a sagittal cross section and
FIG. 3 shows an exploded view of a first embodiment;
FIG. 4 shows a variant of the first embodiment;
FIG. 5 shows a sagittal cross section and
FIG. 6 shows an exploded view of a second embodiment;
FIGS. 8 and 9 show two sagittal cross sections along section lines B and C, respectively, in FIG. 10.

DETAILED DESCRIPTION OF THE INVENTION

Figure 6:
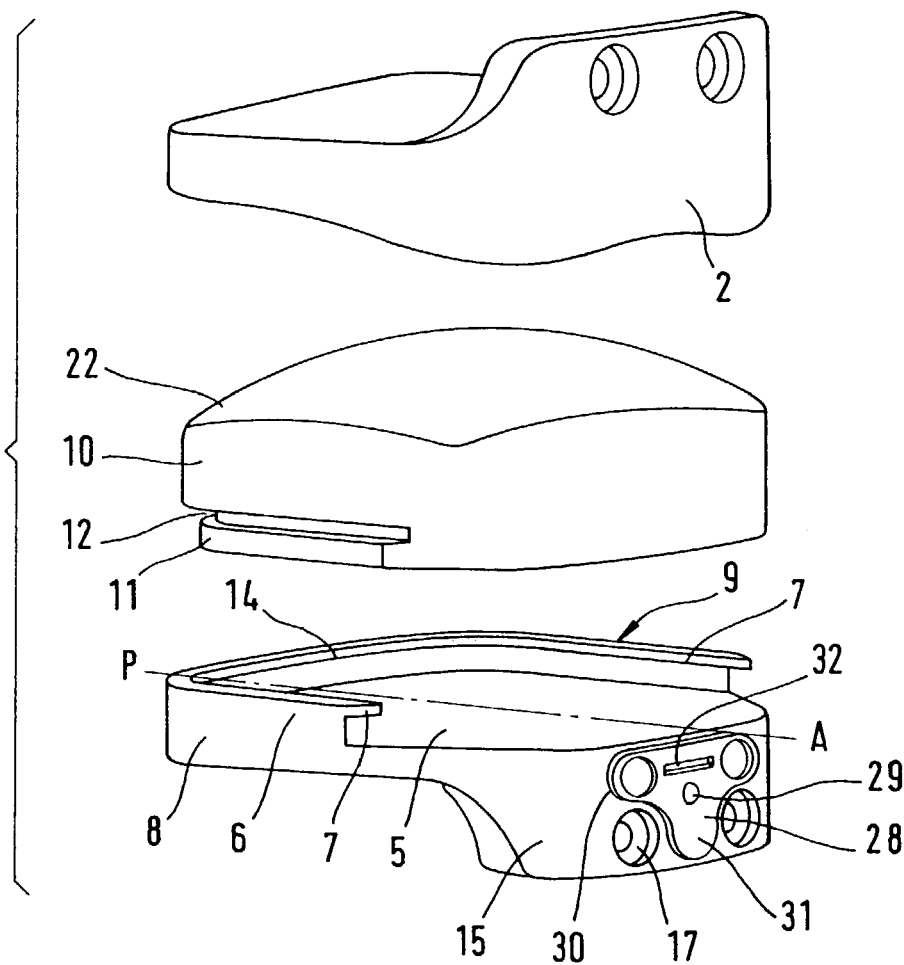

The lower cover plate 1 and the upper cover plate 2 of the first embodiment have outer surfaces 3 and 4, respectively, which are intended for anchoring to the associated vertebral body. They are preferably plane. However, other substantially flat configurations including suitable surface structures for better anchoring to the bone are also conceivable. The cover plates are preferably made of metal.

The lower cover plate 1 has a plane bottom surface 5 facing toward the upper cover plate 2 and enclosed on three sides by a collar 6 which, above an inner undercut, forms an inwardly projecting ridge 7. The lower cover plate 1 is of oval or approximately rectangular shape in plan view.

The bottom surface 5 and the collar 6 of the lower cover plate 1 form a seat for the prosthesis core 10, which is made of a material with good sliding properties, for example polyethylene. It has a plane lower surface which matches the bottom surface 5 and which is delimited laterally and dorsally by an edge ridge 11 above which a groove 12 is situated. The ridge 11 engages in the undercut of the collar 6 below the ridge 7. The ridge 7 engages in the groove 12. By this means, the prosthesis core 10 is secured against lifting from the lower cover plate 1. Sliding play is provided between the collar 6 and the lower cover plate 1 and the edge of the core 10. In the area of their sides 8, 9, the branches of the collar 6 and ridges 7 and 11 and of the groove 12 located there extend parallel to one another and rectilinearly.

In plan view, the core 10 has substantially the same contour shape on all sides as the lower cover plate 1 and the upper cover plate 2. It covers in particular the collar 6, so that the size of the slide surface 22 made available by the upper face of the core is not reduced by the presence of the collar 6. The collar 6 can be made small in relation to the height of the core 10. Nevertheless, the core cannot escape from the space between the cover plates 1 and 2, because it is prevented from lifting from the cover plate 1 by the interaction of the undercut ridges 7 and 11.

On their ventral edge, the cover plates 1, 2 each have a securing flange 15, 16 which issues from them approximately at right angles and which has screw holes 17 for fastening to the vertebral body. Located in the flange 15 of the lower cover plate 1 there is a slot 18 which forms a slide guide for a limit-stop plate 14, which is held displaceably therein. It can assume the locking position shown in FIG. 2 in which it forms a limit stop for the forwardly directed movement of the core 10. It can also be pushed so far down into the slot 18, or completely removed from the latter, to allow the prosthesis core easily to be introduced from the ventral direction into the seat of the lower cover plate and between the cover plates. It has two bores 19 which, in the locking position, are flush with the screw holes 17. When the lower cover plate 1 is secured on the vertebral body via the screw holes 17, the fastening screws also pass through the holes 19 and thus secure the limit-stop plate 14 in its locking position.

The lateral branches of the collar 6, with their ridge 7 interacting with the ridge 11 and the groove 12 of the core 10, form a guide device for the prosthesis core 10 into which the latter can be pushed from the open ventral side (on the right in FIG. 2) in the AP direction (indicated in FIG. 3). The dorsal part 21 of the collar 6 acts as a securing limit stop which prevents the core from escaping in the dorsal direction from the space between the cover plates 1 and 2. The guide function depends on the presence of the undercut on the collar 6 and on the edge of the core 10 only in the lateral areas 8 and 9 of the lower cover plate 1 and of the core 10, and not in the dorsal part 21 of the collar 6.

At its top, the core 10 has a preferably convexly spherical articulation surface 22 which, in order to form an articulation, interacts with the concavely spherical slide surface 23 on the underside of the upper cover plate 2.

Whereas the prosthesis core 10 in the embodiment according to FIG. 2 is fixed immovably between the dorsal limit stop 21 and the ventral limit stop 14 in the mounted state, FIG. 4 shows a variant in which the prosthesis core 10 is a little shorter ventrally (on the right in FIG. 4) than the lower cover plate, so that a clearance remains between its ventral end face 13 and the limit stop 14 when the prosthesis core is situated in its farthest dorsal position. In the mounted state, the core 10 can move in the AP direction by the value of this clearance. Upon flexion movement, the upper cover plate 2 pivots slightly clockwise in relation to the lower cover plate 1 in the view according to FIG. 4, and upon extension movement it moves in the opposite direction. If the upper cover plate 2 exactly follows the direction predetermined by the slide surfaces 22, 23, this pivot movement is associated with a translation movement which is directed forwardly upon flexion (toward the right in FIG. 4) and directed rearwardly upon extension (toward the left in FIG. 4). Part of this translation movement may be inconsistent with the physiological situation and may lead to undesired stresses. These stresses cause restoring forces which, in the prosthesis design according to the invention, result in the upper cover plate moving in the opposite direction relative to the lower cover plate and thereby compensating for the undesired component of movement.

Between the interacting guide devices of the core and of the cover plate, so much clearance can be left in the lateral direction that a certain relative movement is possible also in this direction.

In a cervical spine prosthesis, the extent of the movement clearance in the AP direction is preferably between one and four, more preferably of the order of two to three millimeters. If a relative mobility in the lateral direction is provided, the extent of this should not be more than two millimeters.

For the second illustrative embodiment, the above description applies except for the ventral limit stop. On their ventral edge, the cover plates 1, 2 each have a flange 15, 16 which issues from them at right angles and which has screw holes 17 for fastening to the vertebral body. On the flange 15 of the lower cover plate 1, a limit-stop plate 28 is secured pivotably by means of a headed pin 29, centrally between two screw holes 17. The plane in which it can slidably pivot is defined by the front face of the securing flange 15, which is therefore referred to as slide-guide surface. The limit-stop plate has two wings 30 extending substantially sideward, and a tongue 31 extending transverse to these. It is made of resilient metal and is prestressed in such a way that its wings 30 press against the slide-guide surface. For engagement of a turning tool, for example a screw driver, it has a suitable opening or depression 32. When it is located in the mounting position shown in FIG. 6, it does not extend above the bottom surface 5 of the lower cover plate. The core 10 can therefore be pushed unimpeded into the insertion guide formed by the collar 6. When it is turned through 180°, as is illustrated in FIGS. 5 and 7, the tongue 31 protrudes above the bottom surface 5 and thus forms a limit stop which prevents the core 10 from leaving the guide toward the ventral side.

In the mounting position shown in FIG. 6, the limit-stop plate 28 leaves the screw holes 17 free for engagement of the fastening screws. As is shown in FIG. 7, the wings 30 completely or partially cover the screw holes 17 in the securing position and press elastically on the screw heads located in these in order to prevent them from leaving the screw holes 17. They have an opening which, under prestressing, engages over the caps of the screw heads 33 indicated in FIG. 7 and thus prevents the securing plate from leaving the securing position.

Figure 7:
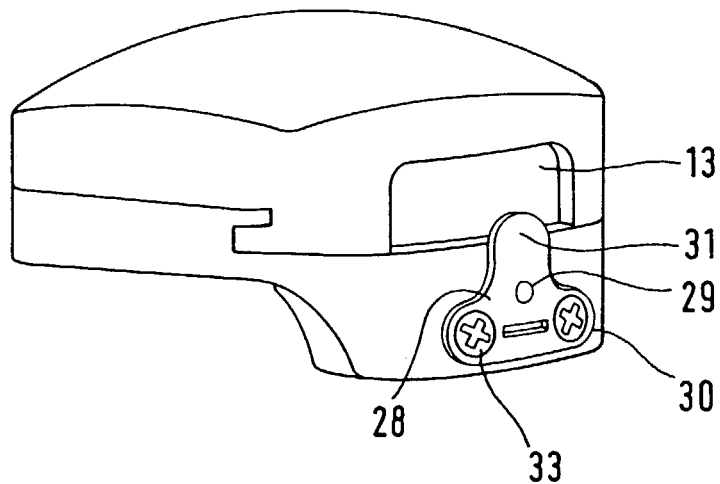
FIG. 7 shows the second embodiment with limit-stop plate switched round.

As is indicated in FIG. 7, a free space of a few millimeters can be located between the tongue 31 of the limit-stop plate 28, provided as limit stop for the prosthesis core 10, and that surface 13 of the core 10 lying opposite it. By this means, the core 10 can move a certain distance in the AP direction in the guide formed by the lateral portions 8, 9 of the collar 6 (see description of FIG. 4). If this movement clearance is not wanted, the free space between the surface 13 and the limit stop 14 is reduced to zero, as is assumed to be the case in FIG. 6.

For the third embodiment according to FIGS. 8 through 12, the above description of FIGS. 1 through 3 also applies, except for the ventral limit-stop device.

Figure 10:
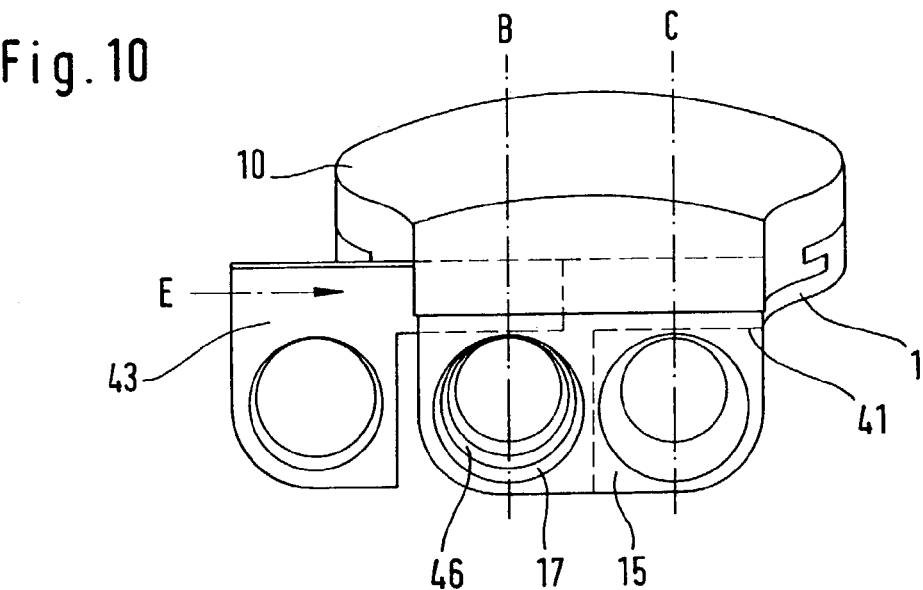
FIGS. 10 and 11 show two perspective views of the third embodiment and
FIG. 12 shows the limit-stop plate of the third embodiment.
Figure 11:
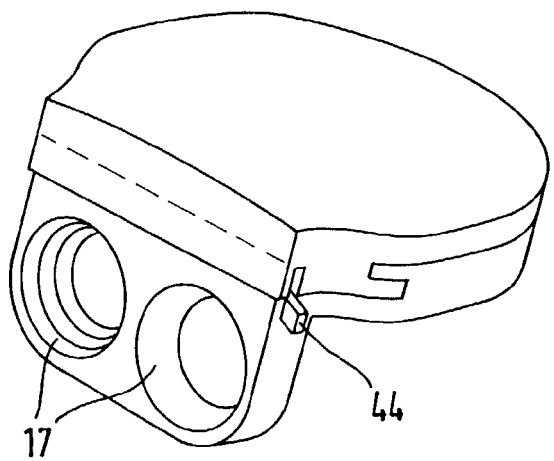

A slot 40, cut-in along the ventral edge of the lower cover plate 1, extends fully from top to bottom in the left half of the flange 15 in FIG. 10 and, in the right part of the flange 15, is delimited by the broken line 41 shown in FIG. 10. Opposite the slot 40, a slot 42 is cut into the underside of the prosthesis core 10 and lies flush with the slot 40. The two slots 40, 42 serve to receive a limit-stop plate 43 whose contour approximately matches the limits of the space which is intended to receive it and which is formed by the slots 40, 42. As FIG. 10 shows, it can be pushed into the slots 40, 42 from the side after the prosthesis core 10 has been inserted.

The limit-stop plate 43 can be provided at the end with a lug 44 which, after complete insertion of the limit-stop plate 43 into the slots 40, 42, protrudes on the right-hand side (see FIG. 11) and can be bent back to secure the limit-stop plate. The flange 15 has screw holes 17 which are used for fastening the lower cover plate 1 on the associated vertebral body. In the left part (see FIG. 10) the screw hole 17 situated there passes through the slot 40, which at that point extends over the full height of the flange 15, in order to receive the left, broad wing 45 of the limit-stop plate. This broad wing 45 of the limit-stop plate likewise has a screw hole 46 which, when the limit-stop plate 43 is pushed in (FIGS. 9 and 11), is flush with the screw hole 17 situated there. When a fastening screw is located in this screw hole, the limit-stop plate 43 cannot escape from its securing position.

Figure 12:
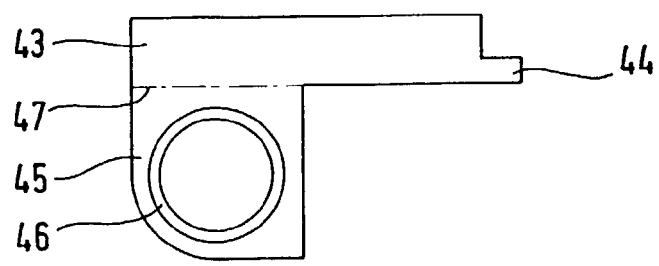

The screw hole 46 and the lug 44 form securing devices which act independently of one another. It is therefore not always necessary for both of them to be provided. If the screw hole 46 is present, the lug 44 can be omitted. If the lug is provided, the broad wing 45 of the limit-stop plate below the line 47 and the corresponding part of the slot in the securing flange 15 can be omitted. It then suffices to have a limit-stop plate which extends above the broken line 47 (FIG. 12). To ensure that the limit-stop plate in this case too cannot escape toward the right from the receiving slots 40, 42, a securing lug (not shown) corresponding to the lug 44 can also be provided at the left-side end of the limit-stop plate 43. The limit-stop plate 43 cannot escape upward because it is covered by that part of the prosthesis core 10 which forms the slot 42.

Figure 13:
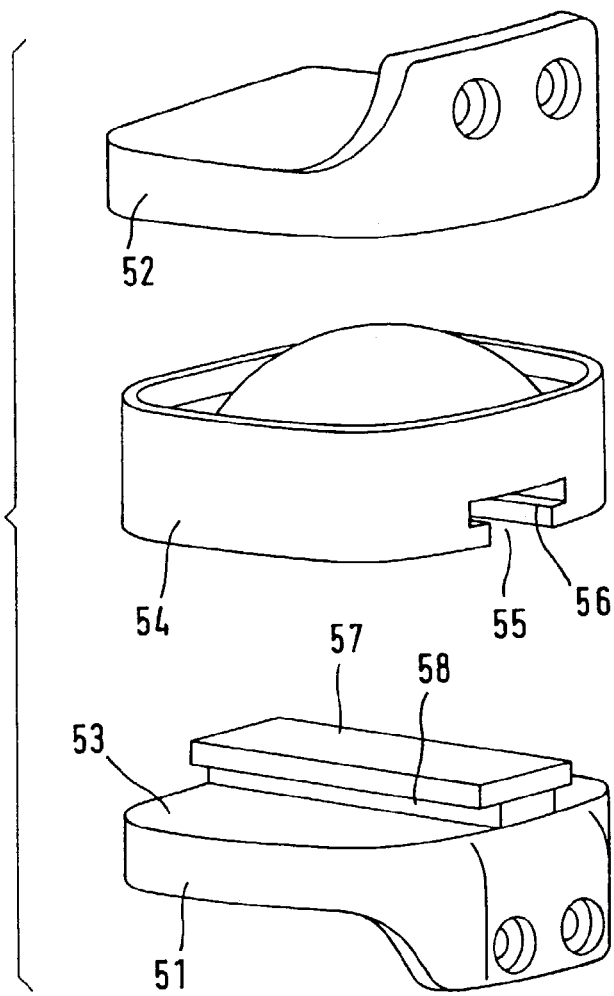
FIG. 13 shows an exploded view of a fourth embodiment and
FIG. 14 shows a variant of the lower cover plate of the fourth embodiment.
Figure 14:
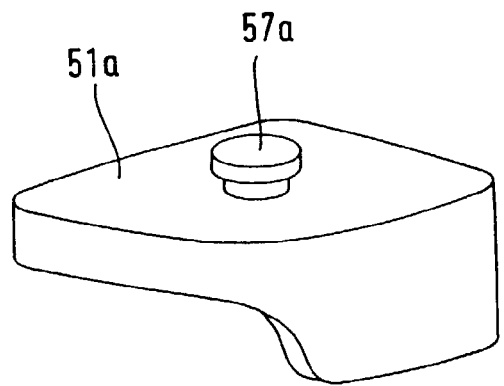

The fourth embodiment according to FIGS. 13 and 14 illustrates an alternative possible configuration of the seat which is formed on the lower cover plate 1 for the prosthesis core 10. In this embodiment, the prosthesis consists of a lower cover plate 51 and an upper cover plate 52. The lower cover plate has an upper, plane bottom surface 53 on which the prosthesis core 54 lies. Whereas this core in the previously discussed embodiments is guided via its outer edges, in the fourth embodiment it has a recess 55 with undercut inner edges 56 which interact with an elongate projection 57 of the lower cover plate with correspondingly undercut edges 58. The core 54 is thus movable in the AP direction relative to the lower cover plate 51, in the same way as was explained with reference to the first illustrative embodiment. In addition, the interaction of the undercuts protects it against lifting from the lower cover plate. Limit stops are provided (not shown) which prevent the prosthesis core from escaping dorsally and ventrally from the space between the plates.

The lower cover plate 51 can be replaced by the lower cover plate 51a which is shown in FIG. 14 and which differs from the lower cover plate 31 in that its projection 57a is not elongate, but circular in plan view. This means that the prosthesis core 54, which is assumed to be connected in terms of rotation to the upper cover plate 52 with respect to a vertical axis, can rotate about the projection 57a without impeding the desired AP movement. This may be desirable in the case of an aspherical configuration of the slide surfaces between core 54 and upper cover plate 52.

What is claimed is:

1. An intervertebral prosthesis, comprising a first cover plate configured to be connected to a first vertebral body, a second cover plate configured to be connected to a second vertebral body, and a prosthesis core which forms an articulation with the second cover plate and is held by a seat of the first cover plate, which seat is designed as a guide device into which the core can be moved from a ventral side relative to the first cover plate, the first cover plate having, on a ventral edge, a slide guide with respect to which a limit stop on the first cover plate is displaceable between a locking position and a nonlocking position and has a height such that the limit stop does not interfere with relative motion between the prosthesis core and the second cover plate, wherein the slide guide is formed by a guide slot which extends transverse to the guide device and which is configured to receive the limit stop and wherein the limit stop is designed as a limit-stop plate.

2. The prosthesis as claimed in claim 1, wherein the guide slot has a guide direction (D) extending transverse to a plane of extension of the first cover plate and the limit-stop plate, which is configured to be movable in guide direction (D) is, in its locking position, partially held in the slot and partially extends above a bottom surface of the first cover plate.

3. The prosthesis as claimed in claim 2, wherein the guide slot is provided in the ventral edge of the first cover plate and in a securing flange arranged thereon.

4. The prosthesis as claimed in claim 2, wherein the guide slot has at least one first screw hole passing through it, and the limit-stop plate has a second screw hole which is flush with the first screw hole when the limit-stop plate is in its locking position.

5. The prosthesis as claimed in claim 4, wherein the limit-stop plate comprises a bendable fastening lug projecting in the guide direction of the guide slot.

6. The prosthesis as claimed in claim 2, wherein the prosthesis core has an articulation surface that covers substantially the entire first cover plate.

7. The prosthesis as claimed in claim 4, wherein the prosthesis core has an articulation surface that covers substantially the entire first cover plate.

8. The prosthesis as claimed in claim 2, wherein the prosthesis core has a slot which is flush with the guide slot and receives part of the limit-stop plate.

9. The prosthesis as claimed in claim 8, wherein the limit-stop plate comprises a bendable fastening lug projecting in the guide direction of the guide slot.

10. The prosthesis as claimed in claim 8, wherein the prosthesis core has an articulation surface that covers substantially the entire first cover plate.

11. The prosthesis as claimed in claim 2, wherein the limit-stop plate comprises a bendable fastening lug projecting in the guide direction of the guide slot.

12. The prosthesis as claimed in claim 1, wherein the guide slot has a guide direction (E) extending parallel to a plane of extension of the first cover plate and transverse to an anterior-posterior direction, and the limit-stop plate can be moved in the anterior-posterior direction into the locking position.

13. The prosthesis as claimed in claim 12, wherein the prosthesis core comprises a part which covers the limit-stop plate held in the guide slot and which prevents the limit-stop plate from leaving the guide slot transverse to guide direction (E).

14. The prosthesis as claimed in claim 13, wherein the prosthesis core has a slot which is flush with the guide slot and receives part of the limit-stop plate.

15. The prosthesis as claimed in claim 12, wherein the guide slot has at least one first screw hole passing through it, and the limit-stop plate has a second screw hole which is flush with the first screw hole when the limit-stop plate is in its locking position.

16. The prosthesis as claimed in claim 12, wherein the limit-stop plate comprises a bendable fastening lug projecting in the guide direction of the guide slot.

17. The prosthesis as claimed in claim 12, wherein the prosthesis core has an articulation surface that covers substantially the entire first cover plate.

18. The prosthesis as claimed in claim 1, wherein the limit-stop plate comprises a bendable fastening lug projecting in the guide direction of the guide slot.

19. The prosthesis as claimed in claim 18, wherein the prosthesis core has an articulation surface that covers substantially the entire first cover plate.

* * * * *